(12) United States Patent
Riley

(10) Patent No.: US 7,198,794 B1
(45) Date of Patent: Apr. 3, 2007

(54) TOPICAL FORMULATION FOR TREATING FINGERNAILS AND TOENAILS

(76) Inventor: Lorri Riley, Rural Route 1, Box 203, Spearfish, SD (US) 55783

( * ) Notice: Subject to any disclaimer, the term of this patent is extended or adjusted under 35 U.S.C. 154(b) by 757 days.

(21) Appl. No.: 10/081,333

(22) Filed: Feb. 22, 2002

(51) Int. Cl.
A61K 8/00 (2006.01)
A61K 9/00 (2006.01)
A01N 25/34 (2006.01)

(52) U.S. Cl. .................. 424/400; 424/61; 424/404
(58) Field of Classification Search .......... 424/61, 424/401, 443
See application file for complete search history.

(56) References Cited

U.S. PATENT DOCUMENTS

| | | | |
|---|---|---|---|
| 4,696,946 A * | 9/1987 | Green et al. ............ 514/574 |
| 5,304,724 A | 4/1994 | Newton | |
| 5,861,142 A | 1/1999 | Schick | |
| 5,951,990 A * | 9/1999 | Ptchelintsev ............ 424/401 |
| 6,117,118 A | 9/2000 | Laughlin et al. | |
| 6,183,763 B1 | 2/2001 | Beerse et al. | |
| 6,231,840 B1 | 5/2001 | Buck | |
| 6,231,875 B1 | 5/2001 | Sun et al. | |
| 6,821,523 B2 * | 11/2004 | Maibach et al. ............ 424/400 |
| 6,846,837 B2 * | 1/2005 | Maibach et al. ............ 514/350 |

* cited by examiner

*Primary Examiner*—S. Tran
(74) *Attorney, Agent, or Firm*—J. David Wharton; Stinson Morrison Hecker LLP

(57) ABSTRACT

A topical formulation for treating toenails and fingernails is provided. This formulation includes a mixture of calcium hydroxide, sodium hydroxide, an antifungal agent, and an applicating agent. The formulation is topically applied to a patient's fingernail or toenail to treat a fungal infection, to remove discoloration, and/or to thin an overly thick nail.

15 Claims, No Drawings

TOPICAL FORMULATION FOR TREATING FINGERNAILS AND TOENAILS

STATEMENT REGARDING FEDERALLY SPONSORED RESEARCH OR DEVELOPMENT

Not Applicable.

CROSS-REFERENCE TO RELATED APPLICATIONS

Not Applicable.

BACKGROUND OF THE INVENTION

The present invention relates to a formulation for treating fungal infections. More specifically, this formulation is a topical formulation for use on fingernails and toenails.

Many people have fingernails or toenails with fungus underneath. Still others have nails that are extremely thick even approaching approximately 1 inch in thickness. Still others have yellowed or discolored nails. Some have combinations of the above-mentioned conditions.

Some medications available for treating these unsightly conditions are not able to kill fungal infections underneath the nail because they are not able to penetrate the nail. Still other medications cause the nail to become brittle. In addition, other medications simply do not work. Therefore, many people are unable to remove these unsightly conditions.

In order to overcome the disadvantages of medications currently available, a formulation that is able to penetrate the nail to kill fungus without permanently damaging the nail is needed. This formulation should be able to be applied topically.

SUMMARY OF THE INVENTION

It is an object of the present invention to provide a formulation for killing fungus on or underneath toenails or fingernails so that the appearance of the nails is improved.

It is a further object of the present invention to provide a method of administering a topical nail formulation so as to rid a person of a nail fungal infection.

According to the present invention, the foregoing and other objects are achieved by a topical formulation for treating fungus on or beneath toenails and fingernails. This formulation includes a mixture of calcium hydroxide, sodium hydroxide, an antifungal agent, and an applicating agent. The formulation is topically applied to a patient's fingernail or toenail to treat a fungal infection or to thin an overly thick nail.

Additional objects, advantages, and novel features of the invention will be set forth in the description that follows and in part will become apparent to those skilled in the art upon examination of the following, or may be learned by practice of the invention.

DETAILED DESCRIPTION OF THE PREFERRED EMBODIMENT

The formulation of the present invention is an effective topical treatment for fighting fungal infections, removing discoloration, and/or thinning overly thick nails. It is used for treating deformed, disfigured or discolored toenails and fingernails. This formulation includes a mixture of calcium hydroxide, sodium hydroxide, an antifungal agent, and an applicating agent. Antibiotics may also be added to the formulation. The formulation is made by mixing these components together.

The calcium hydroxide and sodium hydroxide in the formulation function to penetrate the nail so that the antifungal medication may contact any fungal infection underneath the nail and/or so as to thin the nail. Preferably, the calcium hydroxide and sodium hydroxide are present in the formulation in about a 40:60 to 60:40 ratio by weight. Most preferably, these components are present in approximately a 50:50 ratio by weight.

The antifungal agent may be any agent that is able to kill fingernail and toenail fungus. Preferably, the antifungal medication is benzalkonium chloride, which is able to kill nail fungus upon contact.

The applicating agent may be an ointment, a lotion, nail polish, or combinations thereof. If nail polish is used as the applicating agent, preferably, it is clear nail polish. The ointment that may be used in the formulation of the present invention includes, but is not limited to, oxyquinoline, petrolatum, lanolin, glycerine, or combinations thereof.

The calcium hydroxide is about 0.5 to 50% by weight of the formulation. Preferably, it is about 0.5 to 30% by weight of the formulation. Most preferably, it is about 0.5 to 8% by weight of the formulation.

The sodium hydroxide is about 0.5 to 50% by weight of the formulation. Preferably, it is about 0.5 to 30% by weight of the formulation. Most preferably, it is about 0.5 to 8% by weight of the formulation.

The antifungal agent is about 0.5 to 80% by weight of the formulation. Preferably, it is about 5 to 50% by weight of the formulation. Most preferably, it is about 20 to 35% by weight of the formulation.

The applicating agent is about 20 to 95% by weight of the formulation. Preferably, it is about 30 to 80% by weight of the formulation. Most preferably, it is about 40 to 75% by weight of the formulation.

If the formulation of the present invention is formulated to be obtained over-the-counter, it most preferably should include about 5% by weight of a calcium hydroxide and sodium hydroxide mixture, about 20% by weight benzalkonium chloride, and about 75% by weight applicating agent. If this formulation is formulated to be prescribed by a physician, then most preferably, it should include about 15% by weight of a mixture of calcium and sodium hydroxide, about 25% by weight benzalkonium chloride, and about 60% by weight applicating agent.

The formulation is made by mixing calcium hydroxide, sodium hydroxide, an antifungal agent, and an applicating agent together. No heating or cooling is required in making the formulation. Preferably, the formulation is made by first combining the calcium hydroxide and sodium hydroxide into a mixture. The calcium hydroxide and sodium hydroxide mixture is then added to the applicating agent. The antifungal agent is then added to the mixture. The mixture is agitated or stirred to form the formulation of the present invention.

The formulation of the present invention may be used to treat nails with fungus thereon or underneath, yellowed nails, nails with other discolorations, and/or nails that are overly thick, such as nails that are approximately ¼ to 1 inch thick.

In use, a patient applies an emollient to the skin surrounding the affected nail. The emollient may be, but is not limited to, an antibiotic ointment or petroleum jelly. Next, the formulation is applied directly to the affected nail so as to cover the nail. Following application of the formulation, a bandage is placed over the nail. The formulation is applied approximately once per day. If irritation is noticed, it may be applied once every other day. It can be applied for up to about 6 months.

When treating thick nails, they can be thinned in approximately 2 to 3 weeks. When treating nails with fungus thereunder, the actual antifungal effect is not seen for 4 months to 1 year, the time frame for a nail to completely grow out and be replaced.

The present invention provides a topical treatment for thick nails due to fungus or other causes. It has been found to be able to penetrate the nail and reduce the thickness of the nail without causing major debrittlement. Also, the antifungal medication in the product is able to penetrate the nail and rid the nail of fungal infections beneath the nail.

The following example describes a formulation of the present invention and a method of using this formulation. The formulation and method are within the scope of this invention. This example is not meant in anyway to limit the scope of this invention.

EXAMPLE 1

A topical nail formulation was prepared by mixing calcium hydroxide, sodium hydroxide, benzalkonium chloride, and ointment together. The formulation contained 7.5% by weight calcium hydroxide, 7.5% by weight sodium hydroxide, 25% by weight benzalkonium chloride, and 60% by weight ointment.

An elderly woman had a thick fungus infected toenail for approximately 15 years. She was unable to wear shoes for more than a couple of hours because they were uncomfortable. Furthermore, her toenail would damage her shoes. Her toenail was approximately ¾ of an inch thick. After 1½ weeks of applications, her toenail was thinned down to a normal thickness. Following this, she was able to wear her shoes all day long.

From the foregoing, it will be seen that this invention is one well adapted to attain all the ends and objects herein above set forth together with other advantages which are obvious and inherent to the formulation. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

We claim:

1. A topical nail formulation, comprising the mixture of:
    calcium hydroxide;
    sodium hydroxide;
    an antifungal agent; and
    an applicating agent selected from the group consisting of lotion, ointment, nail polish, and combinations thereof
    wherein said formulation is about 0.5 to 50% by weight calcium hydroxide, about 0.5 to 50% by weight sodium hydroxide, about 0.5 to 80% by weight an antifungal agent, and about 20 to 95% applicating agent.

2. The formulation of claim 1, wherein said formulation is about 0.5 to 30% by weight calcium hydroxide, about 0.5 to 30% by weight sodium hydroxide, about 5 to 50% by weight an antifungal agent, and about 30 to 80% by weight ointment.

3. The formulation of claim 1, wherein said formulation is about 0.5 to 8% by weight calcium hydroxide, about 0.5 to 8% by weight sodium hydroxide, about 20 to 35% by weight an antifungal agent, and about 40–75% ointment.

4. A topical nail formulation, comprising the mixture of:
    calcium hydroxide;
    sodium hydroxide;
    an antifungal agent;
    an applicating agent selected from the group consisting of lotion, ointment, nail polish, and combinations thereof; and
    an effective quantity of an antibiotic, wherein said formulation is about 0.5 to 50% by weight calcium hydroxide, about 05 to 50% sodium hydroxide, about 0.5 to 80% by weight an antifungal agent, and about 20 to about 95% applicating agent.

5. A method of making a topical nail formulation, comprising:
    providing calcium hydroxide, sodium hydroxide, an antifungal agent, and an applicating agent in a formulation comprising about 0.5 to 50% by weight calcium hydroxide, about 05 to 50% sodium hydroxide, about 0.5 to 80% by weight an antifungal agent, and about 20 to about 95% applicating agent, said applicating agent being selected from the group consisting of lotion, ointment, nail polish, and combinations thereof;
    mixing said calcium hydroxide and said sodium hydroxide to form a mixture;
    adding said mixture to said applicating agent; and
    adding said antifungal agent to said mixture to form said topical nail formulation.

6. The method of claim 5, further comprising:
    adding an effective quantity of an antibiotic to said topical nail formulation.

7. A method for treating a nail of a patient, comprising:
    providing a formulation comprising: calcium hydroxide; sodium hydroxide; an antifungal agent; and an applicating agent selected from the group consisting of lotion, ointment, nail polish, and combinations thereof, wherein said formulation is about 0.5 to 50% by weight calcium hydroxide, about 05 to 50% sodium hydroxide, about 0.5 to 80% by weight an antifungal agent, and about 20 to about 95% applicating agent; and
    applying said formulation to a nail of a patient in need thereof.

8. The method of claim 7, wherein said formulation is applied approximately daily for at least about two weeks.

9. The method of claim 7, wherein said nail is at least about 3 inch thick and wherein said formulation thins said nail.

10. The method of claim 7, wherein said nail has a fungal infection and wherein said formulation treats said fungal infection.

11. The method of claim 7, further comprising:
    providing an emollient; and
    applying said emollient to skin surrounding said nail before applying said formulation to said nail.

12. The method of claim 11, wherein said emollient is selected from the group consisting of lotion, antibiotic ointment, petroleum jelly, and combinations thereof.

13. The method of claim 7, further comprising:
    providing a bandage; and
    covering said nail with said bandage after applying said formulation.

14. The formulation of claim 1, wherein said applicating agent is an ointment selected from the group consisting of oxyquinoline, petrolatum, lanolin, glycerin, and combinations thereof.

15. The formulation of claim 1, wherein said applicating agent is clear nail polish.

\* \* \* \* \*

UNITED STATES PATENT AND TRADEMARK OFFICE
CERTIFICATE OF CORRECTION

PATENT NO. : 7,198,794 B1  Page 1 of 1
APPLICATION NO. : 10/081333
DATED : April 3, 2007
INVENTOR(S) : Lorri Riley It is certified that error appears in the above-identified patent and that said Letters Patent is hereby corrected as shown below:

Column 4,
Line 45, delete "3 inch thick" and insert -- $1/4$ inch thick -- therefor.

Column 4,
Line 60, delete "wherein said applicating agent is an ointment selected" and insert -- wherein said ointment is selected -- therefor.

Signed and Sealed this

Second Day of October, 2007

JON W. DUDAS
*Director of the United States Patent and Trademark Office*